United States Patent
Cohen et al.

(10) Patent No.: US 11,641,088 B2
(45) Date of Patent: May 2, 2023

(54) PHASED-ARRAY MASER DETECTOR FOR SYNTHETIC APERTURE INTERFEROMETRIC IMAGING

(71) Applicant: Emad Eskandar, Swampscott, MA (US)

(72) Inventors: James Joseph Cohen, Wenham, MA (US); Emad N. Eskandar, Swampscott, MA (US)

(73) Assignee: Emad Eskandar, Swampscott, MA (US)

( * ) Notice: Subject to any disclaimer, the term of this patent is extended or adjusted under 35 U.S.C. 154(b) by 193 days.

(21) Appl. No.: 17/148,275

(22) Filed: Jan. 13, 2021

(65) Prior Publication Data

US 2021/0218214 A1 Jul. 15, 2021

Related U.S. Application Data

(60) Provisional application No. 62/961,263, filed on Jan. 15, 2020.

(51) Int. Cl.
*H01S 4/00* (2006.01)
*H01S 1/04* (2006.01)
(Continued)

(52) U.S. Cl.
CPC ............ *H01S 1/04* (2013.01); *A61B 18/1815* (2013.01); *A61B 90/36* (2016.02); *A61N 5/045* (2013.01);
(Continued)

(58) Field of Classification Search
CPC ... H01S 1/04; H01S 1/005; H01S 1/02; H01S 1/06; H01S 4/00; A61B 18/1815;
(Continued)

(56) References Cited

U.S. PATENT DOCUMENTS

| 3,283,147 A | 11/1966 | Avakian |
| 9,042,413 B1 | 5/2015 | Brown |

(Continued)

FOREIGN PATENT DOCUMENTS

| WO | 2018026424 | 2/2018 |
| WO | 2019021002 | 1/2019 |

(Continued)

OTHER PUBLICATIONS

Anderson, et al. Observation of Bose-Einstein Condensation in a Dilute Atomic Vapor, Science, Jul. 14, 1995, New Series, vol. 269, No. 5221, pp. 198-201.

(Continued)

*Primary Examiner* — Richard Tan
(74) *Attorney, Agent, or Firm* — Andrus Intellectual Property Law, LLP

(57) ABSTRACT

A phased-array MASER detector for synthetic aperture interferometric three-dimensional imaging. The detector elements, for example $10^2$-$10^6$ zero bias Schottky detector diodes with sufficient sensitivity to reliably detect various values of MASER radiation, are arranged in layers offset in three dimensions. The phased-array MASER detector is particularly useful for detecting characteristics in a biological object using low energy (2-10 Watts), coherent MASER radiation. MASER intensity data of an interferometric pattern is collected by the detector array, is deconvolved, and is used to generate three-dimensional energy activity maps for a given time slice or on a time-shifting basis.

12 Claims, 7 Drawing Sheets

(51) Int. Cl.

| | | |
|---|---|---|
| *H01S 1/02* | (2006.01) | |
| *H01S 1/00* | (2006.01) | |
| *A61B 90/00* | (2016.01) | |
| *A61B 18/18* | (2006.01) | |
| *A61N 5/04* | (2006.01) | |
| *H01S 1/06* | (2006.01) | |
| *A61B 18/00* | (2006.01) | |
| *A61N 5/02* | (2006.01) | |

(52) U.S. Cl.
CPC ............... *H01S 1/005* (2013.01); *H01S 1/02* (2013.01); *H01S 1/06* (2013.01); *H01S 4/00* (2013.01); *A61B 2018/0016* (2013.01); *A61B 2018/00446* (2013.01); *A61B 2018/00577* (2013.01); *A61B 2018/1861* (2013.01); *A61B 2090/374* (2016.02); *A61B 2090/3762* (2016.02); *A61N 2005/027* (2013.01)

(58) Field of Classification Search
CPC ............ A61B 90/36; A61B 2018/0016; A61B 2018/00446; A61B 2018/00577; A61B 2018/1861; A61B 2090/374; A61B 2090/3762; A61N 5/045; A61N 2005/027
USPC ........................................................ 331/94.1
See application file for complete search history.

(56) References Cited

U.S. PATENT DOCUMENTS

| | | |
|---|---|---|
| 9,966,720 B2 | 5/2018 | Liu et al. |
| 2003/0098979 A1 | 5/2003 | Dress et al. |
| 2006/0262876 A1 | 11/2006 | LaDue |
| 2009/0287274 A1 | 11/2009 | De Ridder |
| 2012/0289763 A1 | 11/2012 | Boyden et al. |
| 2013/0335706 A1 | 12/2013 | Schmitt-Manderbach et al. |
| 2015/0214687 A1 | 7/2015 | Oxborrow |
| 2017/0367613 A1 | 12/2017 | Eckert et al. |
| 2019/0117109 A1 | 4/2019 | Grundfest et al. |
| 2019/0252842 A1 | 8/2019 | Breeze et al. |

FOREIGN PATENT DOCUMENTS

| | | |
|---|---|---|
| WO | 2019202114 | 10/2019 |
| WO | 2019222436 | 11/2019 |

OTHER PUBLICATIONS

Asbell, et al. Conductive Keratopasty for the Correction of Hyperopia, TR Am Ophth Soc 2001; 99:79-87.
Bauch, Andreas Caesium atomic clocks: function, performance and applications, Meas. Sci. Technol. 14 1159.
Bond, et al. Interferometer techniques for gravitational-wave detection, Living Rev. Relativ (2016) 19:3.
Breeze, et al. Continuous-wave room-termperature diamond maser, Mar. 22, 2018, vol. 555, Nature, pp. 493-500.
Covey, et al. Illicit Dopamine Transients: Reconciling Actions of Abused Drugs Trends Neurosci. Apr. 2014.
Dirac, The Quantum Theory of the Emission and Absorption of Radiation, St. John's College, Cambridge and Institute for Theoretical Physics, Copenhagen, Feb. 2, 1927.
Einstein, A. The Quantum Theory of Radiation Mar. 1917.
Gordon, et al. The Maser-New Type of Microwave Amplifier, Frequency Standard, and Spectrometer, Physical Review, vol. 99, No. 4, Aug. 15, 1955.
Hernandez-Lopez, et al. D1 Receptor Activation Enhances Evoked Discharge in Neostriatal Medium Spiny Neurons by Modulating an L-Type Ca2+ Conductance, The Journal of Neuroscience, May 1, 1997 17(9):3334-3342.
Hoppe, et al. Laser interstitial thermotherapy (LiTT) in epilepsy surgery, British Epilepsy Association, Feb. 16, 2017.
Hubel, et al. Receptive Fields and Functional Architecture of Monkey Striate Cortex, J. Physiol. (1968) 195, pp. 215-243.
Mach, L. Via an interference refractory, Mar. 1892 (machine translation included).
Maiman, T.H. Stimulated Optical Radiation in Ruby, Nature Aug. 6, 1960 vol. 187 pp. 493-494.
Miloni et al. Laser Physics, Wiley & Sons, Inc. 2010.
Mountcastle, Vernon B. Modality and Topographic Properties of Single Neurons of Cat's Somatic Sensory Cortex, Department of Physiology, The Johns Hopkins University School of Medicine, Nov. 5, 1956.
Patel, et al. Studying task-related activity of individual neurons in the human brain, Nature Protocols, vol. 8 No. 5, 2013 pp. 949-957.
Reid, Macgregor S. Low-Noise Systems in the Deep Space Network, Jet Propulsion Laboratory, California Institute of Technology, Feb. 2008.
Reinstein, et al. Short term LASIK outcomes using the Technolas 217C excimer laser and Hansatome microkeratome in 46 708 eyes treated between 1998 and 2001, Br J Opthalmol 2012; 96:1173-1179.
Schawlow, et al. Infrared and Optical Masers, Physical Review, vol. 112, No. 6, Dec. 15, 1958 pp. 1940-1949.
Schuliz, et al. Responses of Monkey Dopamine Neurons During Learning of Behavioral Reactions, Journal of Neurophysiology, vol. 67, No. 1, Jan. 1992 pp. 145-163.
Schultz, et al. Responses of Monkey Dopamine Neurons to Reward and Conditioned Stimuli during Successive Steps of Learning a Delayed Response Task, The Journal of Neuroscience, Mar. 1993, 13(3): 900-913.
Schultz, et al. Dopamine neurons report an error in the temporal prediction of reward during learning, Nature America Inc., Nature Neuroscience, vol. 1 No. 4, Aug. 1998 pp. 304-309.
Wu, et al. Modeling the Pulse Signal by Wave-Shape Function and Analyzing by Synchrosqueezing Transform, May 26, 2016.
International Search Report dated Apr. 7, 2021 in co-pending PCT application PCT/US2021/013261.
International Search Report dated Apr. 7, 2021 in co-pending PCT application PCT/US2021/013269.
International Search Report dated Apr. 6, 2021 in co-pending PCT application PCT/US2021/013279.

PHASED-ARRAY MASER DETECTOR FOR SYNTHETIC APERTURE INTERFEROMETRIC IMAGING

FIELD OF THE INVENTION

The invention pertains to a phased-array MASER detector for synthetic aperture interferometric three-dimensional imaging. The detector elements, for example $10^2$-$10^6$ zero bias Schottky detector diodes with sufficient sensitivity to reliably detect various values of MASER radiation, are arranged in layers offset in three dimensions. The phased-array MASER detector is particularly useful for detecting characteristics in a biological object using low energy (2-10 Watts), coherent MASER radiation.

BACKGROUND OF THE INVENTION

The invention is motivated by current advancements with room-temperature MASER technology, including Applicant's co-pending pending application Ser. No. 17/148,120, entitled "Acquisition of Interferometric Recordings of Brain and Neuron Activity by Coherent Microwave Probe with Therapeutic Activation, Inactivation, or Ablation of Molecular, Neuronal or Brain Targets." by Emad N. Eskandar and James Joseph Cohen, filed on even date herewith and incorporated by reference herein; and co-pending application Ser. No. 17/148,215, entitled "Thin Film MASER Emitter and Thin Panel Phased Array of Emitters." by James Joseph Cohen and Emad N. Eskandar, filed on even date herewith and also incorporated herein by reference.

An example of an application in which a detector array constructed and operated in accordance with the invention is useful is a system providing a low-power (2-10 Watt) continuous wave MASER beam to "paint" a 3-Dimensional activity map unto a structural map generated by 3D CT or MRI. This activity map is based on the interplay between a probe MASER beam, resonant frequencies of molecules of the object being imaged, and the interference patterns detected when the probe MASER beam is mixed with a reference MASER beam. The following description provides background on the underlying scientific principles and technology relevant to the invention.

Electromagnetic Radiation (EMR). Visible light is part of the electromagnetic spectrum, which ranges from radio waves to gamma rays. Electromagnetic radiation waves, as their names suggest are fluctuations of electric and magnetic fields, which can transport energy from one location to another. Visible light is not inherently different from the other parts of the electromagnetic spectrum with the exception that the human eye can detect visible waves. Electromagnetic radiation can also be described in terms of a stream of photons which are massless particles each travelling with wavelike properties at the speed of light. A photon is the smallest quantity (quantum) of energy which can be transported. Electromagnetic radiation covers the range from radio waves to hard x-rays, which are also called gamma rays, see FIG. 1. Microwaves have a longer wavelength than visible light waves, as shown in FIG. 1.

Interaction of EMR with Matter. The interaction of electromagnetic radiation (EMR) and matter is central to current imaging techniques and to the invention. EMR is conveyed by photons. The frequency of a photon is proportionate to its energy:

$$E = h\nu = hc/\lambda$$

wherein E is energy, h is Planck's constant, ν is frequency, c is the speed of light, and λ is the wavelength. Simply put, the higher frequency of the photon, the greater its energy.

Electromagnetic radiation interacts with matter through a limited number of mechanisms: transmission (including refraction and diffraction), reflection, absorption, or emission. Transmission implies that photons pass through a substance with minimal interaction, as is the case of visible light passing through a non-opaque gas. Refraction is a function of the different speeds with which electromagnetic radiation is transmitted through different substances; whereas diffraction describes its behavior as it passes through narrow apertures or around edges. Reflection describes the circumstance where an incident beam of electromagnetic radiation encounters a reflective surface such that the resultant beam has an angle equal to the incident beam. Absorption refers to a specific interaction between a photon and an atom or a molecule and emission refers to the discharge of a photon from an atom or a molecule.

At one end of the EMR spectrum are X-rays representing high-energy and high-frequency photons. Interaction of such a photon with an atom is associated with considerable energy transfer. If a photon in the x-ray band of the spectrum interacts with an atom, it causes an electron to be completely ejected from its shell, ionizing the host atom, disrupting its covalent bonds, and potentially damaging or breaking molecules including strands of DNA. At the opposite end of the spectrum are radio-waves, which are composed of low-energy, low-frequency photons. Photons in the radio-wave region of the spectrum generally have weak interactions with biological molecules and are transmitted through without change to either the photon or the molecules (FIG. 1).

Photons in visible light interact with biological molecules primarily through absorption and reflection. Visible light does not transmit through the body, meaning that photons are either reflected or absorbed. Reflected photons give rise to the color of biological tissues, whereas absorbed photons add kinetic energy, or heat, to animal tissues. Microwave emissions occupy a portion of spectrum between visible light and radio-waves and have properties of both. Depending on the frequency, microwaves can interact with biological molecules through, absorption and emission (as with visible light) or can be transmitted (as with radio-waves).

Spontaneous Absorption & Emission. Quantum Physics describes the behavior of atoms and electrons in relation to discrete quanta or packets of energy. Table 1 below provides definitions of a number of terms pertaining to quantum physics.

TABLE 1

| Term | Definition |
| --- | --- |
| Ground State | An atom with its electrons at their lowest orbital is said to be in its Ground State |
| Excited State | An atom is in a higher energy state than its ground state reflecting electrons being in higher orbitals |
| Spontaneous Absorption | Electron transitions from lower energy to higher energy orbital by absorbing a photon or heat |
| Spontaneous Emission | Electron transitions from higher energy to a lower energy orbital by emitting a photon |
| Stimulated Emission | Electron is stimulated by photon to transition from higher to lower energy by emitting another photon |
| Coherence | Photons have the same frequency and phase in stimulated emission |

Electrons can absorb or release energy in the form photons or heat. However, electrons are constrained to occupy discrete orbitals at specific energy levels. Electrons can transition from a lower orbital to higher orbitals through absorbing a photon with a frequency equal to the difference in energy between two orbitals in a process called spontaneous absorption. Excited electrons relax back to their preferred lower energy levels by emitting photons having a frequencies equal to the difference in energy between two orbitals through the process of spontaneous emission (Dirac & Bohr, 1927). Excitation into higher energy states can be only induced only by photons with the requisite frequency. Similarly, relaxation emits photons with the specific frequency corresponding to the particular transition.

Atomic and Molecular Transitions. The state of an electron can be described by four quantum numbers—the principal quantum number or orbital n (orbital), the azimuthal quantum number $\ell$ (subshell), the magnetic quantum number $m_l$ (magnetic moment) and the spin quantum numbers. The energy of an electron is determined by its orbital and subshell. The Pauli exclusion principle states that no two electrons in an atom can have the same values for all four quantum numbers, though it is possible for electrons to have different quantum numbers but have the same energy levels, which are called degenerate orbitals.

Electrons can become excited and transiently occupy higher energy orbitals through the absorption of photons or heat. Relaxation of electrons can occur through radiative decay with the emission of photons, or through non-radiative decay with the emission of heat.

At the level of atoms, spontaneous absorption can occur with photon frequencies in the ultraviolet, visible, and infra-red range of the spectrum. Electron relaxation may occur through a series of smaller steps associated with emission of photons with lower energy and frequency including those in the micro-wave range. The energy of an atom is also a quantum state and reflects the quantum states, as defined by the four quantum numbers, of all its constituent electrons. Molecules have additional degrees of freedom, beyond the four quantum numbers, that are described as molecular vibration and rotation. Transitions between these states are also quantal and generally occur through the absorption and emission of photons with frequencies in the infra-red or microwave range.

Transitions between different quantum energy state can be represented using Jablonski diagrams. An atom or molecule in the lowest energy state possible, known as the ground state, can absorb a photon with a specific frequency whereby it becomes excited and attains a higher energy state FIG. 2A. A substance made of such atoms will absorb this characteristic frequency, and likely other specific frequencies, thereby imparting its color. The atom or molecule tends not to stay in this excited state and relaxes back to its ground state in several ways. In FIG. 2A, the atom or molecule relaxes in two quantum steps, through an intermediate quantum state, and emits two photons both of which have lower frequency and energy than the absorbed photon. The photons emitted will be characteristic for the energy transitions appropriate for that particular atom or molecule, and by studying the light emission the matter under investigation can be determined.

In FIG. 2B, the excited atom or molecule initially loses energy not emitting a photon but by a non-radiative process (heat) emission, to reach an intermediate state. The atom or molecule then relaxes from the intermediate energy state to the ground state by the emission of a lower energy photon than originally absorbed. A uniform collection of atoms or molecules can relax through a combination of mechanisms, the distribution of which, depends on the lifetime of the different intermediate states and external factors such as magnetic fields.

Stimulated Emission. The fundamental idea behind the process called stimulated emission was first described in 1917 as part of a more extensive paper by Albert Einstein on "The Quantum Theory of Radiation" (Einstein, 1917). In stimulated emission, an excited electron is stimulated by an incident photon, not into a higher orbital but rather into a lower orbital, see FIG. 3. In this case, the incident photon is not absorbed, but rather induces the excited electron back into its preferred lower-energy ground or state. This downward transition of the electron results in the emission of a photon. Initially, there are two quanta—the excited electron and the incident photon. Subsequently, there are also two quanta—the incident photon and the emitted photon. Hence, energy is conserved. Critically, however, after the encounter both the incident photon and the emitted photon, having been transiently enmeshed, emerge having the same phase and frequency. Thus, there are three important features to this process. 1) Before emission, the incident photon has a frequency equal to the difference in energy between the excited state and the lower energy state. 2) After emission, both the incident and emitted photon are coherent, having the same frequency, phase, and direction. 3) The process starts with one photon having the requisite frequency to generate an emission and ends with two photons having the necessary frequency to evoke an emission. These two coherent photons can stimulate other atoms potentially leading to 4 coherent photons, which could lead to 8 coherent photons etc.

Hence, under the right circumstances and with a source of energy, this can be to a self-reinforcing or multiplicative process. Upon reaching the lasing or masing threshold, this process creates a surfeit of coherent photons having the same frequency, phase, and direction—a LASER beam for visible light or—a MASER beam—for microwaves. Such beams have unique properties and applications that cannot be realized with incoherent light or microwave radiation, which has a mixture of frequencies, phases, and directions.

The present invention pertains to the use of low-power MASER radiation to record the ability of specific locations in a biological object, such as a human brain, to absorb or release energy between quantum states. More specifically, the present invention pertains to a phased-array MASER detector for synthetic aperture interferometric three-dimensional imaging.

Coherent Synthetic Aperture Detection. In a typical flat-panel detector array, the elements are strictly arranged in two dimensions—similar to tiles on a floor. In contrast, synthetic aperture/interferometric imaging information is derived by correlating intensity and phase information from groups of detectors. For N detectors, there are N (N−1)/2 detector pairs corresponding to N (N−1)/2 pixels in a reconstructed image. In essence, unlike typical arrays where the number of detectors equals the number of pixels, the number of pixels increases by the square of the number of detectors, meaning that fewer detectors and faster frame rates are possible for a desired resolution compared with either a raster-scan or an N detector focal plane array. However, it is necessary to correlate evaluations from different groups of detectors in order to realize this advantage, which entails aperiodic and/or multidimensional detector arrangements.

As an example, consider the two types of arrays for imaging with a set resolution at a given distance using the same number of detectors and a fixed area corresponding to an even number of arbitrary pixels. For the sake of this math that number shall be set to be 1596. The number of detectors is chosen to be N=57, so that the number of pixels in the image is the same for both the focal plane array image (with scanning) and the interferometric imaging method. The focal plane array, at a rate of 57 pixels per scan, would need 28 scans to cover the entire area. In this estimate, it is assumed that the time to digitize or acquire the data from each detector is the same for both the interferometric and the focal plane array approach. This is a reasonable assumption, for example, if the same or comparable detectors are used for both the approaches and the correlation calculations are not a rate-limiting step. The interferometric imaging array can record the entire image with one scan. However, there is a tradeoff—1596 correlations are needed to reconstruct the interferometric image. This correlation hardware requirement is not necessary with a focal plane array. In essence, one is trading imaging speed for backend image processing.

If there is no time restriction to generate an image, one can reduce the required number of detectors for interferometric imaging accordingly. For example, if the aperiodic interferometric array is angled, the equivalent number of pixels in the reconstructed image is $M*N(N-1)/2$ where M is the number of unique rotational positions of the array. Assuming 28 different rotation positions for the interferometric array, the corresponding time to acquire an image would be the same for both the techniques. However, to maintain the number of pixels at 1596, only 11 detectors are required in the interferometric approach compared with 57 for the focal plane array. This reduction in the number of detectors reduces the required number of correlations from 1596 to 55. Thus, if there are technical limitations or difficulty in fabricating focal plane detector arrays with a large number of detectors, synthetic aperture approaches, such as interferometric imaging, can reduce the number of required detectors while maintaining the same number of image pixels.

Synthetic-Aperture Imaging (SAI) is a form of imaging that is used to create two-dimensional images or three-dimensional reconstructions of objects. SAI uses the motion or the dimensional displacement of the detector over a target region to provide finer spatial resolution than conventional array or detector scanning. SAI detectors are typically mounted on a moving platform, such as an aircraft or spacecraft. The technology has its origins in an advanced form of side looking airborne radar (SLAR). The distance the SAI device is displaced or travels over a target in the time taken for the radar pulses to return to the antenna creates the large synthetic aperture (the size of the detector). Typically, the larger the aperture, the higher the image resolution will be, regardless of whether the aperture is physical (a large detector) or synthetic (a moving detector array)—this allows SAI to create high-resolution images with comparatively small physical or 2 dimensional detector arrays. Additionally. SAI has the property of having larger apertures for more distant objects, allowing consistent spatial resolution over a range of viewing distances.

To create an SAI image, successive pulse trains are transmitted to "illuminate" a target, and the convolved mixed interferometric beam is received and recorded. The beams are transmitted and the convolved beams are received using single beam-forming mixers. As the SAI device is scanned, the detector relative to the target changes with time. Signal processing of the successive recorded pulse trains allows the combining of the recordings from these multiple detector positions. This process forms the synthetic antenna aperture and allows the creation of higher-resolution images than would otherwise be possible with a given 2-dimensional static array. SAI is capable of high-resolution remote sensing, as SAI can select frequencies to avoid signal attenuation. SAI has continuous imaging capability as illumination is provided by the Synthetic Aperture emitter.

Synthetic Aperture images have wide application in remote sensing and mapping. Applications of SAI include topography, oceanography, glaciology, geology (for example, terrain discrimination and subsurface imaging), and forestry, including forest height, biomass, deforestation. Volcano and earthquake monitoring use differential interferometry to detect subtle changes in elevation. SAI can also be applied for monitoring civil infrastructure stability such as bridges. SAI is useful in environment monitoring such as oil spills, flooding, urban growth, global change and military surveillance, including strategic policy and tactical assessment. SAI can be implemented as inverse SAI by observing a changing or moving target over a substantial time with a stationary antenna.

A synthetic-aperture detector is an imaging system mounted on a moving platform, or on a 3-D detector array accessible in a temporally regular fashion. Electromagnetic waves are transmitted sequentially, the modulated beam, scatters or echoes are collected, and the system stores the data for subsequent processing. As transmission and reception occur at different times, they map to different positions. The well-ordered combination of the received signals builds a virtual aperture that is much larger than the physical detector array. That is the source of the term "synthetic aperture." giving it the property of an imaging system. The range direction is parallel to the 3-dimensional offset and perpendicular to the azimuth direction.

Basic principle. The 3D processing is done in two stages. The azimuth and range direction are focused for the generation of 2D (azimuth-range) high-resolution images, after which a digital elevation model (DEM) is used to measure the phase differences between complex images, which is determined from different look angles to recover the height information. This height information, along with the azimuth-range coordinates provided by 2D SA focusing, gives the third dimension, which is the elevation. The first step requires only standard processing algorithms. The second step requires additional pre-processing such as image co-registration and phase calibration.

In addition, multiple baselines can be used to extend 3D imaging to the time dimension. Four dimensional and multi-dimensional SAR imaging allows imaging of complex scenario and has improved performance with respect to classical interferometric techniques such as persistent scatter interferometry.

The SAI algorithm, as given here, generally applies to phased arrays. A three-dimensional array (a volume) of scene elements is defined, which will represent the volume of space within which targets exist. Each element of the array is a cubical voxel representing the probability (or "density") of a scattering surface being at that location in space.

Initially, the SAI algorithm gives each voxel a density of zero. Then for each captured waveform, the entire volume is iterated. For a given waveform and voxel, the distance from the position represented by that voxel to the detector(s) used to capture that waveform is calculated. That distance is represented as time delay of the waveform. The sample value at that position in the waveform is then added to the voxel's density value. This represents a possible signal from a target at that position. Note there are several optional approaches here, depending on the precision of the waveform timing, among other things. For example, if phase cannot be accurately determined, only the envelope magnitude (with the help of a Hilbert transform) of the waveform sample might be added to the voxel. If waveform polarization and phase are known and are sufficiently accurate, then these values might be added to a more complex voxel that holds such measurements separately.

After all waveforms have been iterated over all voxels, the basic SAI processing is complete. What remains, in the simplest approach, is to decide what voxel density value represents a solid object. Voxels whose density is below that threshold are ignored. Note that the threshold level must be higher than the peak energy of any single wave, otherwise that wave peak would appear as a sphere (or ellipse, in the case of multi-static operation) of false "density" across the entire volume. Thus, to detect a point on a target, there must be at least two different antenna echoes from that point. Consequently, there is a need for large numbers of detectors positions to properly characterize a target. The voxels that passed the threshold criteria are visualized in 2D or 3D. Optionally, added visual quality can sometimes be had by use of a surface detection algorithm like marching cubes.

Synthetic Aperture via Phased Array Control. Provided that the wave propagating emitter is stable and controllable, the well-established principles of phased array beamforming may be utilized to synthesize a diffraction limited MASER beam with a determinate numerical aperture.

Since the MASER emitters preferably emit diffraction limited energy isotropically, it is necessary to synthetically create a wave front that has selective directionality and mode locked character adequate for the contemplated pass length. Regardless of the source, the principles underlying wave addition may be applied.

Shifted emission phased array principles have been widely used in radar, sonar, seismology, oceanology, and medical imaging. Simply stated, a "phased array" is a group of emitters or sensors located at distinct spatial locations in which the relative phases of the signals are varied in such a way that the overall gestalt propagation mode is reinforced in a selectable direction and deconstructed in all other directions. The phased array principles have allowed the development of emitter and detector assembly's that can beam form and beam steer without any mechanical control.

Phased arrays can act as both wave transmitters (emitters) and wave receivers (detectors). When a phased array works in transmission mode, the relative amplitude of the signals radiated by the array in different directions determines the effective radiation pattern of the array. In practice, a phased array may be used to point toward a fixed direction, or to scan rapidly in azimuth or elevation.

The array acts as a spatial filter, attenuating all signals except those propagating in certain directions. "Beamforming" is the name given to a wide variety of array-processing algorithms that are used to focus the array's signal-receiving or signal-transmitting abilities in a particular direction. A beam refers to the main lobe of the directivity pattern. Beamforming can apply to transmission from the array, to reception in the array, or to both. A beamforming algorithm points the array's spatial filter toward desired directions. This is similar to the dish antenna of conventional radar swiveling to steer its beam into a desired direction; however, the phased-array beam-steering is achieved algorithmically rather than physically. The beamforming algorithm generally performs the same operations on the sensors' signals regardless of the number of sources or the character of the noise present in the wave field.

A phased array system requires fine frequency and phase coherence to a specific and stable operating mode. That may be achieved by a variety of means or by the use of a coherent emitter such as a maser. Symbolically all phased arrays of any integer plurality of emitters (N) is an example of N-slit diffraction provided that the EMR field at the detection point is a consequence of the coherent addition of N point sources in a line.

Since each emitter behaves as a slit diffractor or a point isotropic radiator the diffraction pattern can be derived by summing the phase shift $\varphi$ to the fringing term.

Starting with N-slit diffraction pattern with N slits of equal size and spacing d $$\psi = \psi_0 \frac{\sin\left(\frac{\pi\alpha}{\lambda}\sin\theta\right)}{\frac{\pi\alpha}{\lambda}\sin\theta} \frac{\sin\left(\frac{N}{2}kd\sin\theta\right)}{\sin\left(\frac{kd}{2}\sin\theta\right)}$$

Fringe effects must be included: therefore, it is necessary to add the $\varphi$ term to the kd sin $\theta$ to produce:

$$\psi = \psi_0 \frac{\sin\left(\frac{\pi\alpha}{\lambda}\sin\theta\right)}{\frac{\pi\alpha}{\lambda}\sin\theta} \frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}$$

The intensity of the wave is calculated by taking the square of the wave function.

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{N}{2}\left(\frac{2\pi d}{\lambda}\sin\theta + \phi\right)\right)}{\sin\left(\frac{\pi d}{\lambda}\sin\theta + \frac{\phi}{2}\right)}\right)^2$$

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{\pi}{\lambda}Nd\sin\theta + \frac{N}{2}\phi\right)}{\sin\left(\frac{\pi d}{\lambda}\sin\theta + \frac{\phi}{2}\right)}\right)^2$$

For convenience it assumed that the emitters are separated by $$d = \frac{\lambda}{4}$$

apart (any scalar fraction of the wavelength would function as well).

$$I = I_0 \left(\frac{\sin\left(\frac{\pi\alpha}{\lambda}\sin\theta\right)}{\frac{\pi\alpha}{\lambda}\sin\theta}\right)^2 \left(\frac{\sin\left(\frac{\pi}{4}N\sin\theta + \frac{N}{2}\phi\right)}{\sin\left(\frac{\pi}{4}\sin\theta + \frac{\phi}{2}\right)}\right)^2$$

Sine achieves its maximum value at $$\frac{\pi}{2},$$

thus, the numerator of the second term=1.

$$\frac{\pi}{4}N\sin\theta + \frac{N}{2}\phi = \frac{\pi}{2}$$

$$\sin\theta = \left(\frac{\pi}{2} - \frac{N}{2}\phi\right)\frac{4}{N\pi}$$

$$\sin\theta = \frac{2}{N} - \frac{2\phi}{\pi}$$

As N gets large, the result will be overshadowed by the $$\frac{2\phi}{\pi}$$

term. In a oscillatory system, it is expected that sine will oscillate between −1 and 1, therefore setting $$\phi = -\frac{\pi}{2}$$

will provide the maximum energy on an angle derived by $$\phi = \sin^{-1}1 = \frac{\pi}{2} = 90°$$

If an adjustment to the angle at which the maximum energy is emitted is required, it is only necessary to adjust the phase shift φ between successive emitters.

This technique can control any amount of paired integer elements in a phased array emission device. It is through this means that a nascent isotropic room temperature MASER oscillator can have a plurality of similar devices organized and controlled to produce a coherent beam of extremely large and stable characteristics. Inversely, a similarly active detector array will be able to deconstruct such a beam in order to get information that would otherwise be lost in the diffraction blur.

Interferometry. Interference patterns are generated when two mode-locked wave trains or MASER beams coincide. If the two coincident beams have the same frequency and phase, the result is constructive interference, reinforcing the amplitudes. If they are out of phase, by H period, the result is destructive interference. Other combinations result in more complex, but interpretable, interference patterns. Interferometers are instruments that use this property for very precise measurements of processes occurring from the astronomical scale down to the microscopic scale (Bond et al., 2016). The Mach-Zehnder interferometer configuration is flexible and commonly used (Mach, 1892). The basic principle is to start with one laser beam, which is then split into two beams having the same frequency and phase. One serves as the reference or analyzing beam while the other serves as the probe beam and interacts with the relevant sample. The two beams are then integrated into a single convolved beam. The resultant convolved beam may be analyzed by both digital and analog techniques. Further, the convolved beam may be used as an illumination source for generating a derivative interference pattern that can be analyzed as a 2D or 3D image.

Doppler cooling relies on quantum properties and the well-known Doppler Effect. In a given volume of non-constrained atomic gas above absolute zero, the atoms move randomly in Brownian motion. A source of narrow-band coherent electromagnetic radiation can be deliberately tuned to a frequency slightly lower than that for spontaneous absorption of a favorable transition. Because of the Doppler effect, an atom randomly moving toward the source could experience the radiation as occurring at a slightly higher frequency than that of the beam, potentially its absorption frequency, absorb a photon, and transition to a higher energy state (FIG. 4). Once that electron relaxes back to its ground state, after a few nanoseconds, it emits a photon, but at its characteristic emission frequency, which is slightly higher than that of the originally absorbed photon. The small difference in frequency between the absorbed and emitted photons means that the atom loses a very small amount of kinetic energy with each cycle, which is dissipated in the surrounding volume. By using pairs or arrays of opposing beams, it is possible to effectively trap a volume of atoms, so they lose energy in multiple directions of movement. Since each event is very brief, the process can repeat many times in a short period, with the atoms losing kinetic energy over many iterations. This approach has been used to rapidly cool substances close to absolute zero and was critical in the recent demonstration of the Bose-Einstein condensate (Anderson et al, 1995).

Resonant Coupling. Doppler-cooling is an effective demonstration of how coherent emissions can achieve surprising and seemingly counter-intuitive results through their quantum effects. However, the tuning range for Doppler cooling is very narrow and another quantum interaction, resonant coupling, is relevant to one of the uses of the invention. Wave-coupling occurs when two waves are linked in some way so they can transfer energy. Resonance occurs if the two have a common frequency and are at least partially in-phase. An imperfect but helpful analogy is the example of an adult pushing a child on a swing. The swing has a natural frequency of oscillation. After a few pushes, if the adult repeatedly pushes the swing at the same frequency the oscillation, both the adult and the swing are in-phase, and the child goes much higher. An analogous phenomenon can be observed with the behavior of two-level quantum systems in the presence of coherent electromagnetic radiation. For practical purposes, most quantum shifts can be reduced to two-level systems. American physicist Isaac Rabi's derived the formula for estimating the probability of finding such a system in one or the other state, as a function of time see FIG. 5 and the following equations:

$$\Omega = \sqrt{\lambda^2 + (\omega - \omega_{21})^2/4}; P_2(t) = 1 - P_2(t);$$

$$P_2(t) = \left[\frac{\lambda^2}{\lambda^2 + (\omega - \omega_{21})^2/4}\right]\sin^2(\Omega t).$$

These equations and plot in FIG. 5 illustrate the probability of finding one of the states in presence of coherent emission at the resonance frequency (Γ=0) and at increasingly detuned frequencies (Γ=☐/10) . . . wherein Ω is the Rabi frequency, γ is equal to 1 in non-relativistic conditions, (is the frequency of the perturbation, $\omega_{21}$ is the resonance frequency of the system, t is time, $P_1$ is the probability of finding the system in state-1, and $P_2$ the probability of the system being in state-2, and Γ represents different levels of detuning. If the coherent radiation has the same frequency as the resonant frequency, then over time, the system alternates between states 1 and 2 at the frequency of the radiation. Critically, coherent radiation is effective at modulating the probability of states, or transitions, even if the frequency is not exactly the same as the resonant frequency of the molecule, so long as falls within a certain range. Practically, this means that frequency coupling is more forgiving than the Doppler cooling described above.

Diffraction Limits. The Abbe limit is a well settled understanding of the behavior for diffraction-based optics. This holds true for all electromagnetic radiation, which ranges from radio waves to gamma rays, and includes visible light. Electromagnetic radiation waves, as their names suggest are fluctuations of electric and magnetic fields, which can transport energy from one location to another. Visible light is not inherently different from the other parts of the electromagnetic spectrum with the exception that the human eye can detect visible waves. Electromagnetic radiation can also be described in terms of a stream of photons which are massless particles each travelling with wavelike properties at the speed of light. A photon is the smallest quantity (quantum) of energy which can be transported.

The observation of sub-wavelength structures with microscopes is difficult because of the Abbe diffraction limit. Ernst Abbe found in 1873 that electromagnetic oscillatory fields with wavelength $\lambda$, traveling in a medium with refractive index n and converging to a spot with half-angle $\theta$, will have a minimum resolvable distance of $$d = \frac{\lambda}{2n\sin\theta} - \frac{\lambda}{2NA}$$

The portion of the denominator n sin $\theta$ is called the numerical aperture (NA) and can reach about 1.4-1.6 in modern optics, hence the Abbe limit is d=$\lambda$/2.8. Considering green light around 500 nm and a NA of 1, the Abbe limit is roughly d=$\lambda$/2=250 nm (0.25 µm), which is small compared to most biological cells (1 µm to 100 µm), but large compared to viruses (100 nm), proteins (10 nm) and less complex molecules (1 nm). To increase the resolution, shorter wavelengths can be used as in UV and X-ray microscopes. These techniques offer better resolution but are expensive, suffer from lack of contrast in biological samples, and may damage the sample.

Near-field Techniques. The diffraction limit is only valid in the far field as it assumes that no evanescent fields reach the detector. Various near-field techniques that operate at less than ≈1 wavelength of light away from the image plane, can obtain substantially higher resolution. These techniques exploit the fact that the evanescent field contains information beyond the diffraction limit which can be used to construct very high-resolution images, in principle beating the diffraction limit by a factor proportional to how well a specific imaging system can detect the near-field signal. For scattered light imaging, instruments such as near-field scanning optical microscopes peripherally resemble an atomic force microscope. The data recorded by such instruments often requires substantial processing, essentially solving an optical inverse problem for each image.

The use of synthetic aperture techniques in the detector in the subject invention permits the recovery of information well beyond the diffraction limit.

Maser Interaction with Brain in Activity Mapping. The brain represents a complex mixture of organized atoms, molecules, membranes, and cells. However, some of the same considerations related to activity mapping apply. Referring to FIG. 6, neuronal processes such as axons or dendrites are antennas, preferentially coupling MASER radiation to molecules such as voltage-gated ion channels and receptors embedded within the phospholipid bilayer. The brain is not a uniform substance, however. Hence, the disclosed detector system can selectively record activity in specific areas based on a number of features including 1) The pattern of activity, 2) The molecular characteristics of different neurons, 3) The spatial location of neurons in the brain relative to a three-dimensional structural map obtained using conventional 3-D MRI or CT images and 4) The size and configuration of particular neuronal subtypes. Each of these factors affects interaction of the probe beam with the brain. These changes are then detected in the interference pattern generated by recombining the probe beam with the reference beam.

Biological Basis of Neuronal Activity. The basic work of the brain is performed by neurons. A typical neuron has three important elements, the dendritic tree, the soma, and the axon (see FIG. 6). Neurons maintain a resting membrane potential of −70 Mv primarily through the Na+/K+-ATPase, an active molecule in the cell membrane that moves 3 Na+ ions out of the cell and two K+ into the cell for each unit of ATP.

Neurons communicate through the release of neurotransmitters at synaptic junctions. A neuron integrates the excitatory and inhibitory inputs to its dendritic tree, which are generated by synapses from other neurons. If there are enough excitatory potentials at a given time causing the membrane at the take-off of the axon from the soma (the axon hillock) to reach its threshold (−55 Mv), then an action potential is initiated through the local opening of voltage-gated $Na^+$ channels allowing $Na^+$ ions to rush into the cell causing the membrane potential to become transiently positive to a peak of +30 Mv. As the membrane becomes depolarized, voltage-gated $K^+$ channels start to open allowing $K^+$ to leave the cell. Once the Action potential reaches its peak, the Na+ channels close while K+ channels continue to be open, causing the membrane to return to, and slightly exceed, its resting potential (a period called hyper-polarization), during which it is refractory to the generation of action potentials.

Synaptic Vesicle Release. Once an action potential is initiated, adjacent areas of the membrane become depolarized, reach the threshold and depolarize, leading to a wave of depolarization traveling along the axon, away from the soma, in the process of propagation. Once the wave of depolarization reaches the axon terminal it causes voltage-gated $Ca^{++}$ channels to open. The increased intracellular concentration of $Ca^{++}$ causes synaptic vesicles to fuse with the membrane at the synaptic terminal and release their neurotransmitter into the synaptic cleft (FIG. 9). At this point, the neuron under discussion becomes the presynaptic neuron affecting the next postsynaptic neuron.

Neurotransmitters exert their effects through ligand-gated channels that can induce inhibitory or excitatory potentials in the postsynaptic neuron. Ligand-gated channels are critical to neurotransmission and are the targets of a large number of pharmacologic agents as well as substances of abuse.

Molecular Changes Recorded by MASER System. This process of summating inputs, initiating action potentials, and releasing neurotransmitters is the essence of neuronal activity. Most of the critical elements are mediated by conformational changes membrane bound ion channels. This activity based conformational changes are an important signal for MASER activity mapping when the present invention is used to probe the human brain. In addition, the flow of ions in and out of neurons is associated with changes in water volume representing another signal the MASER system can record.

As an example, a detector system constructed in accordance with the invention can be used to differentially record conformational changes in voltage-gated ion channels, ligand-gated ion channels, and G protein coupled receptors. This allows the recording of neuronal activity at the cellular and subcellular level. Moreover, each of these channels and receptors has unique patterns of absorption and emissions that change depending on the conformational state. Thus, a detector system constructed in accordance with the invention can identify neurons having increased, or decreased, activity relative to the background, and also the particular type of channel in play and hence the associated neurotransmitter or ligand.

As another example, neurodegenerative disorders such as Parkinson, Alzheimer, and Huntington's disease, are characterized the accumulation of misfolded protein in neurons. Each disorder is associated with the aggregation of a particular moiety: Alzheimer—B pleated sheets; Parkinson—α Synuclein, and Huntington Disease—Huntingtin. Individual protein molecules are easily broken down and cleared by normal cellular processes. However, once these particular proteins aggregate into increasingly larger pathological aggregates (sheets, folds, fibrils, and tangles) they become insoluble and therefore highly resistant to normal cellular mechanisms for protein degradation. The MASER system disclosed in the incorporated co-pending application Ser. No. 17/148,120, "Acquisition of Interferometric Recordings of Brain and Neuron Activity by Coherent Microwave Probe with Therapeutic Activation, Inactivation, or Ablation of Molecular, Neuronal or Brain Targets," by Emad N. Eskandar and James Joseph Cohen, can selectively energize these pathological aggregates, allowing them to dis-aggregate, at which point they can be cleared by the cells. This would arrest and potentially reverse, the progression of Parkinson disease, Alzheimer disease, and Huntington disease.

Neuronal processes such as axons or dendrites are antennas, preferentially coupling MASER emissions to molecules such as voltage gated ion channels and receptors embedded within the phospholipid bilayer. Most features of neuronal activity, such as depolarization, generation of action potentials, and neurotransmitter release, are mediated through conformational changes of molecules embedded in phospholipid bilayer. Activity mapping, e.g., using a phased array detector system constructed in accordance with the invention, identifies conformational changes and the spatial location of the changes. Molecules susceptible to energy coupling are apparent as spectral absorptions, or as stimulated emissions, occurring during the period of activity. Hence, the map can provide information regarding both the spatial location and the presence of molecular targets for enervation.

SUMMARY OF THE INVENTION

The invention pertains to a phased-array MASER detector and method for synthetic aperture interferometric three-dimensional energy mapping of biological objects, such as the human brain. The detector elements, for example $10^2$-$10^6$ zero bias Schottky detector diodes with sufficient sensitivity to reliably detect intensity of MASER radiation, are arranged in layers offset in three dimensions. The phased-array MASER detector is particularly useful for detecting characteristics in biological objects using low energy (2-10 Watts), coherent MASER radiation.

In one aspect of the invention, a phased-array MASER detector for synthetic aperture interferometric three-dimensional imaging includes an array of detector elements arranged in a first planar layer and in a second planar layer that is parallel to the first planar layer. The detector elements in the second layer are offset in three dimensions from the detectors elements in the first planar layer such that each detector element is able to detect intensity of an interference pattern created by a convolved MASER beam directly. The orthogonal offset of the layers in parallel planes perpendicular to the path of the convolved MASER beam provide spatial discrimination which can be used by a synthetic aperture algorithm as an equivalent to a delay or phase shift, thereby improving processing efficiency. The offset in the exemplary embodiment is such that spatially offset detector elements permit correspondence to a time difference measured in decades of picoseconds. The specific offset distance can be selected depending the characteristics of the MASER radiation expected to be detected.

In the exemplary embodiment, each detector element is zero biased Schottky detector diode that detects the intensity of MASER radiation. Zener diodes are used to zero bias each Schottky detector diode. The phased array detector, with the three-dimensional offset of detector elements in the first and second layer can be fabricated using conventional or slightly modified semiconductor fabrication techniques.

The phased-array detector is configured in particular to sense time-sliced intensity of an interferometric pattern formed by the convolution of a probe MASER beam that passes through an object being analyzed and a reference MASER beam. The system with which the phased-array detector is used also desirably includes a database that stores time-sliced intensity data detected by the detector elements, and a computer configured to deconvolve the time-sliced intensity data in the database at least in part by implementing a synthetic aperture imaging algorithm to create a holographic perspective map. The computer is programmed to populate a voxel map with deconvolved data from multiple perspectives in the holographic perspective map, and to associate the voxel map with an MRI or CT scan to generate a three-dimensional energy activity map for the time slice. This three-dimensional energy activity map for the time slice can be then be displayed for a physician or specialist to view.

In another aspect, the invention pertains to a method of energy activity mapping of a biological object using real-time MASER interferometry. The method starts by emitting a beam of coherent MASER radiation and passing the emitted beam through a collimator. The collimated beam of coherent MASER radiation is then split into a probe beam and a reference beam. The probe beam is passed through a biological object to create a modulated probe beam and the reference beam is simultaneously passed through a uniform substance resulting in a delay of the reference beam similar to that of the probe beam caused by the biological object in order to generate a lagged reference beam. The lagged reference beam and the modulated probe beam are combined to create a convolved beam characterized by a time-shifting interference pattern. The time-sliced intensity data of the interference pattern in the convolved beam is detected with a plurality of detector elements of the phased array detector. The plurality of detector elements in the phased array detector are arranged in a first planar layer and in a second planar layer that is parallel to the first planar layer and offset in three dimensions from the detectors elements in the first planar layer, as described above.

Time-sliced intensity data of the interference pattern detected by the plurality of detector elements is recorded in a database. Then, a computer is programmed to de-convolve the time-sliced intensity data of the interference pattern. It will often be desirable, as the first step of deconvolution, to apply a Fast Fourier Transform in order to isolate one or more wavefront frequencies for processing. The result of the deconvolution results in processed data that quantifies changes in one or more of phase, modulation, amplitude, and lag between the modulated probe beam and the lagged reference beam and the creation of a holographic perspective map. A voxel map is populated with the processed data for the slice of time from the given holographic perspective and this is repeated from multiple holographic perspectives in accordance with a synthetic aperture algorithm to improve the resolution.

The populated voxel map is then associated with or overlayed on an image generated by an MRI or CT scan to create a three-dimensional energy activity map for the given time slice of the biological object or a portion of the biological object. The three-dimensional energy activity map for the given time slice is then displayed for immediate review or stored for later analysis. Then, method can be repeated for subsequent time slices to generate time-shifting, three-dimensional energy activity maps.

While conceptually similar to lasers, a maser produces electromagnetic radiation in the microwave frequency range with longer and less energetic wavelengths than visible light Unlike lasers, masers can penetrate optically opaque tissues. Maser emission does not have the harmful effects of ionizing radiation such as x-rays. By using interferometry, the comparison of a reference beam with a probe beam, the proposed MASER detection system can create three-dimensional energy activity maps of the human brain with an ultra-high degree of spatial resolution. At the theoretical limit, this approach can detect changes in activity with spatial and temporal resolution of 0.3 microns and 10 nanoseconds, respectively. Using real-time deconvolutional hardware and software to capture changes in the interference pattern at a direct resolution of 10 nanoseconds enables a differential resolution theoretically as low as 100 femtoseconds.

The primary object of this invention is to provide practical means for implementing MASER interferometry, and in particular implementing MASER interferometry in biomedical clinical or research applications. MASER interferometry for energy activity mapping is designed for detection of subtle changes in molecular properties, as opposed to structural mapping. In one application, the invention uses coherent MASER emissions to record and convey dynamic changes in brain activity. Coherent microwave emissions are well-matched to the proposed brain mapping activity for several reasons. 1) Photons in the microwave range can be transmitted, absorbed, or emitted by biological molecules. 2) Microwaves interact with biological molecules through the quantum transitions associated with vibration and rotation, meaning that the brain is semi-translucent from the microwave perspective. 4) In communications, antennas are devices having a dipole, or balanced charge. They are used as an interface between electromagnetic radiation and the current within the conductor. Neuronal processes such as axons or dendrites are antennas, preferentially coupling MASER emission to molecules such as voltage-gated ion channels and receptors embedded within the phospholipid bilayer. 5) Most features of neuronal activity such as depolarization, generation of action potentials, neurotransmitter release, depolarization (along with various excitatory and inhibitory currents) are mediated through conformational changes of molecules embedded in phospholipid bilayer. 6) Comparison of a probe beam with a reference beam allows for an exquisite degree of resolution since interferometry can detect minute changes in one beam relative to the other.

7) Interferometry requires far less energy than using one beam to detect differences above the noise. 8) Comparing two beams to another greatly reduces noise. 9) Dynamic interferometry detects and records activity in real-time.

Accordingly, one object of the phase array detector is to enable large scale recording of neuronal brain activity at sub-micron granularity, and a temporal resolution approaching 100 femtoseconds. For example, the object of the phased array detector described herein is to enable MASER dynamic interferometry to record inferred changes to quantum states of sodium and potassium ions, changes in the conformation and energy states of biological molecules such as ion channels, changes in the molecules and membrane potentials of neuronal dendrites, soma, and axons, and changes associated with the neuronal firing of action potentials.

Additionally, it is an object of the invention to provide a phased array detector that enables MASER interferometry to be used to study, characterize, and understand activity patterns associated with normal sensory functions of the brain including but not limited to vision, audition, somatosensory perception, olfaction, and gustatory responses.

Another object of the invention to provide a phased array detector that enables MASER interferometry to be used to study, characterize, and understand energy activity patterns associated with normal output functions of the brain including but not limited reflex movements, simple volitional movements, complex sequences of movements and patterns of behavior.

Another object of the invention to provide a phased array detector that enables MASER interferometry to be used to study, characterize, and understand energy activity patterns associated with normal cognition including but not limited to learning, short-term memory, long-term memory, conflict resolution, social behavior, subjective decision-making and objective and decision making.

Yet another object of the invention to provide a phased array detector that enables MASER interferometry to be used to study, characterize, and diagnose activity patterns associated with behavioral, psychiatric, and neurological brain disorders.

Other objects and advantages of the disclosed invention may be apparent to those skilled in the art upon reviewing the drawings and the description therein.

DETAILED DESCRIPTION

Figure 1:
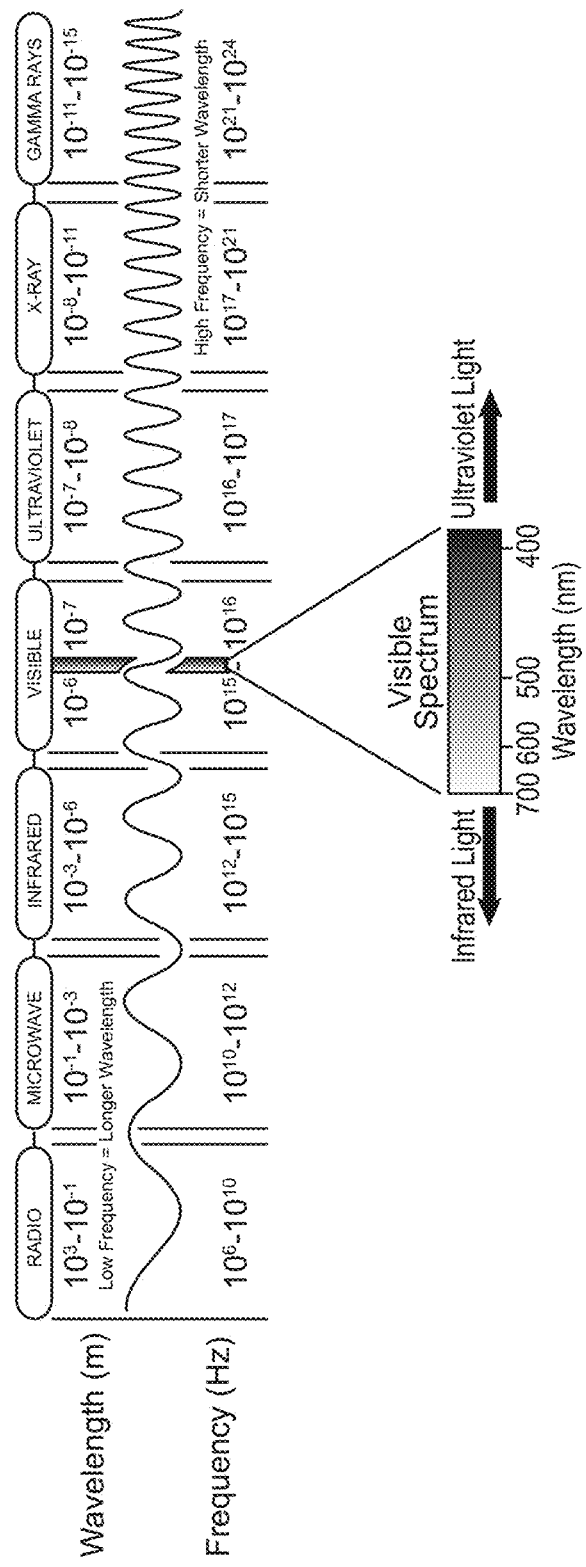
FIG. 1 is a diagram illustrating wavelength and frequency along the electromagnetic spectrum.
Figure 2A:
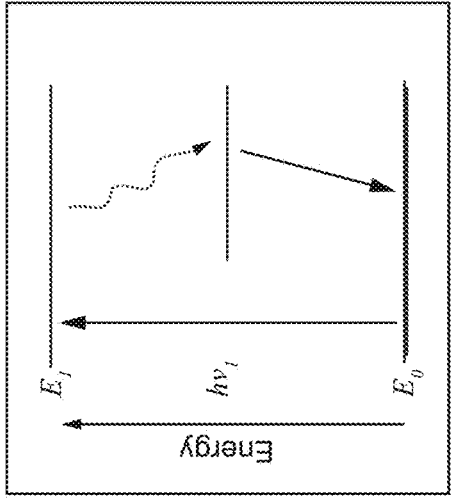
FIGS. 2A and 2B are Jablonski diagrams illustrating the relaxation of a molecule or atom to a lower energy state through emission of photons (FIG. 2A) and relaxation of a molecule or atom to a lower energy state through loss of heat and photon emission (FIG. 2B).
Figure 2B:
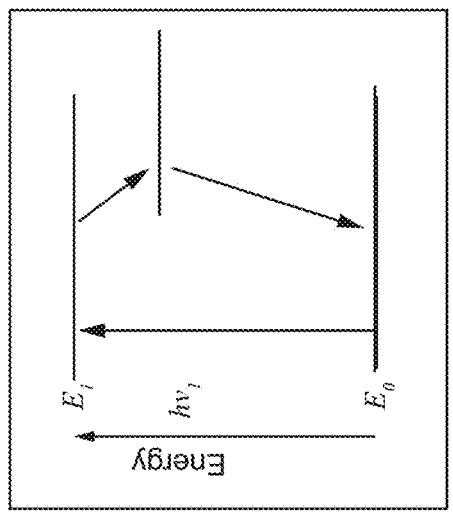
Figure 3:
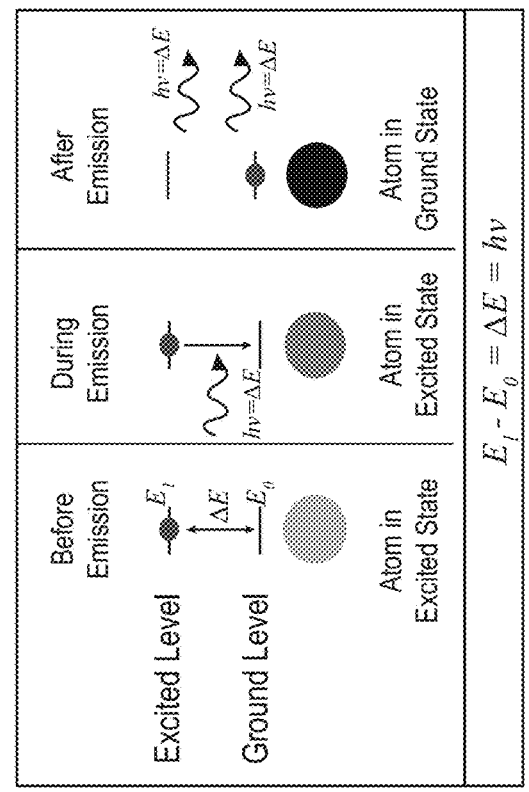
FIG. 3 is a diagram illustrating stimulated emission.
Figure 4:
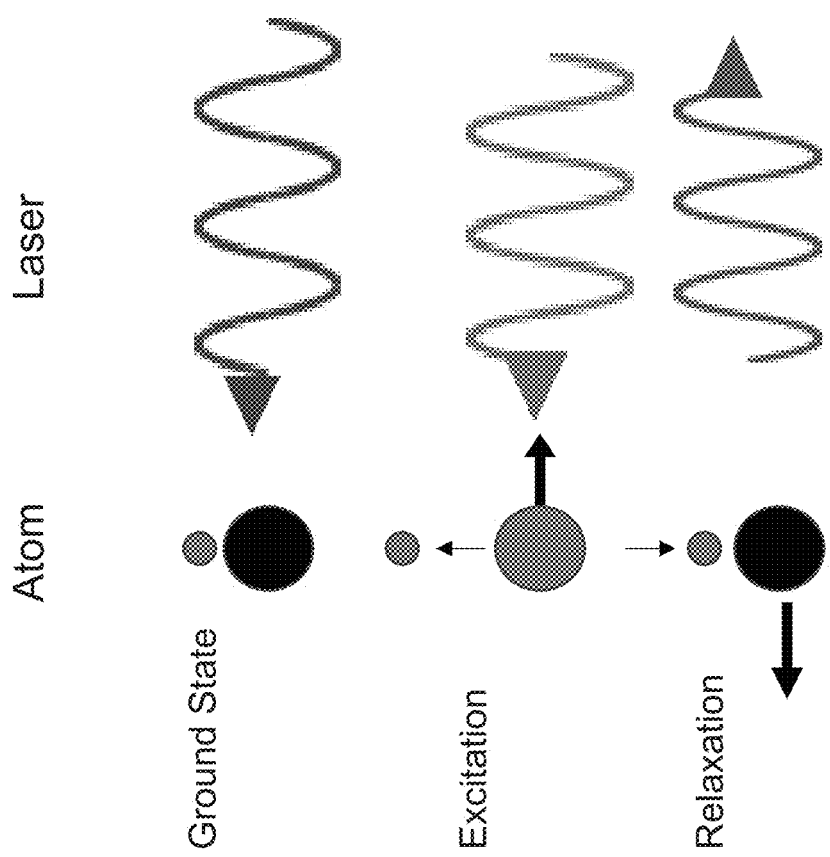
FIG. 4 is a schematic illustration showing doppler cooling by LASER radiation.
Figure 4:
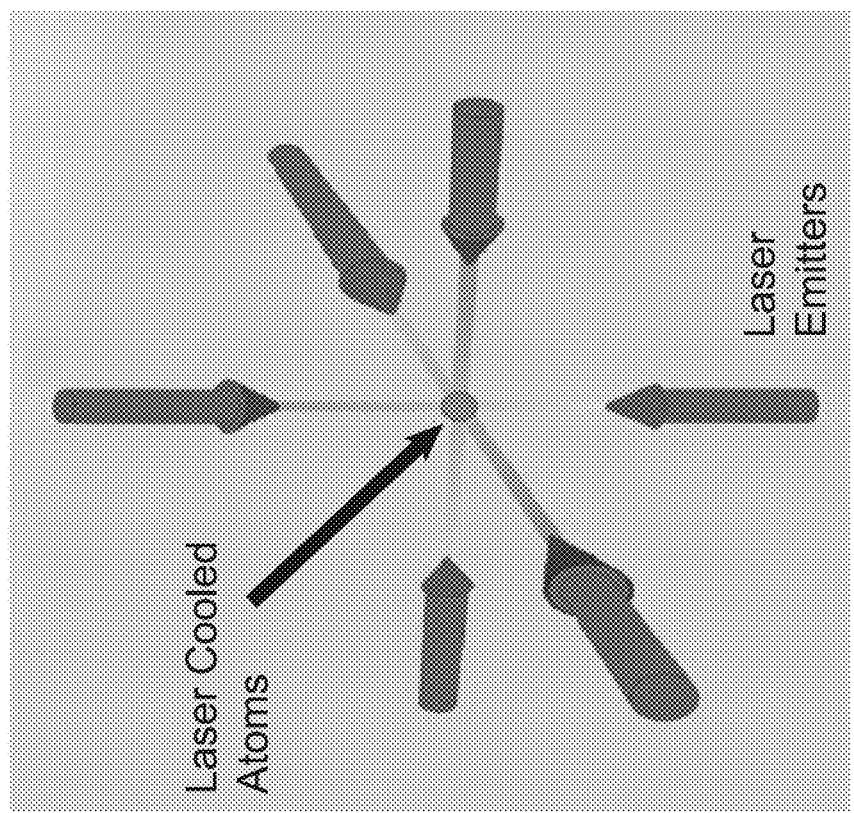
Figure 5:
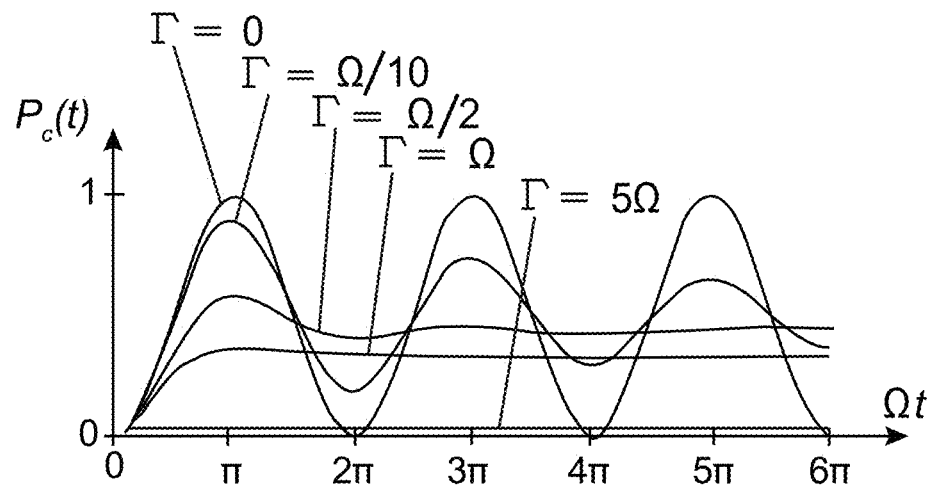
FIG. 5 is a plot illustrating Rabi probability at various frequencies.
Figure 6:
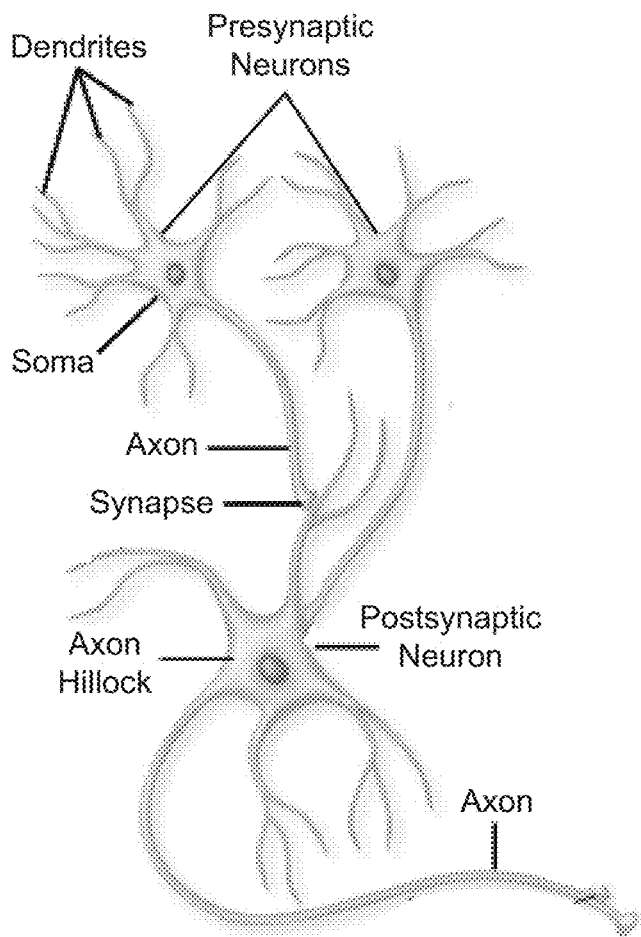
FIG. 6 is a schematic illustration of presynaptic neurons.
Figure 7:
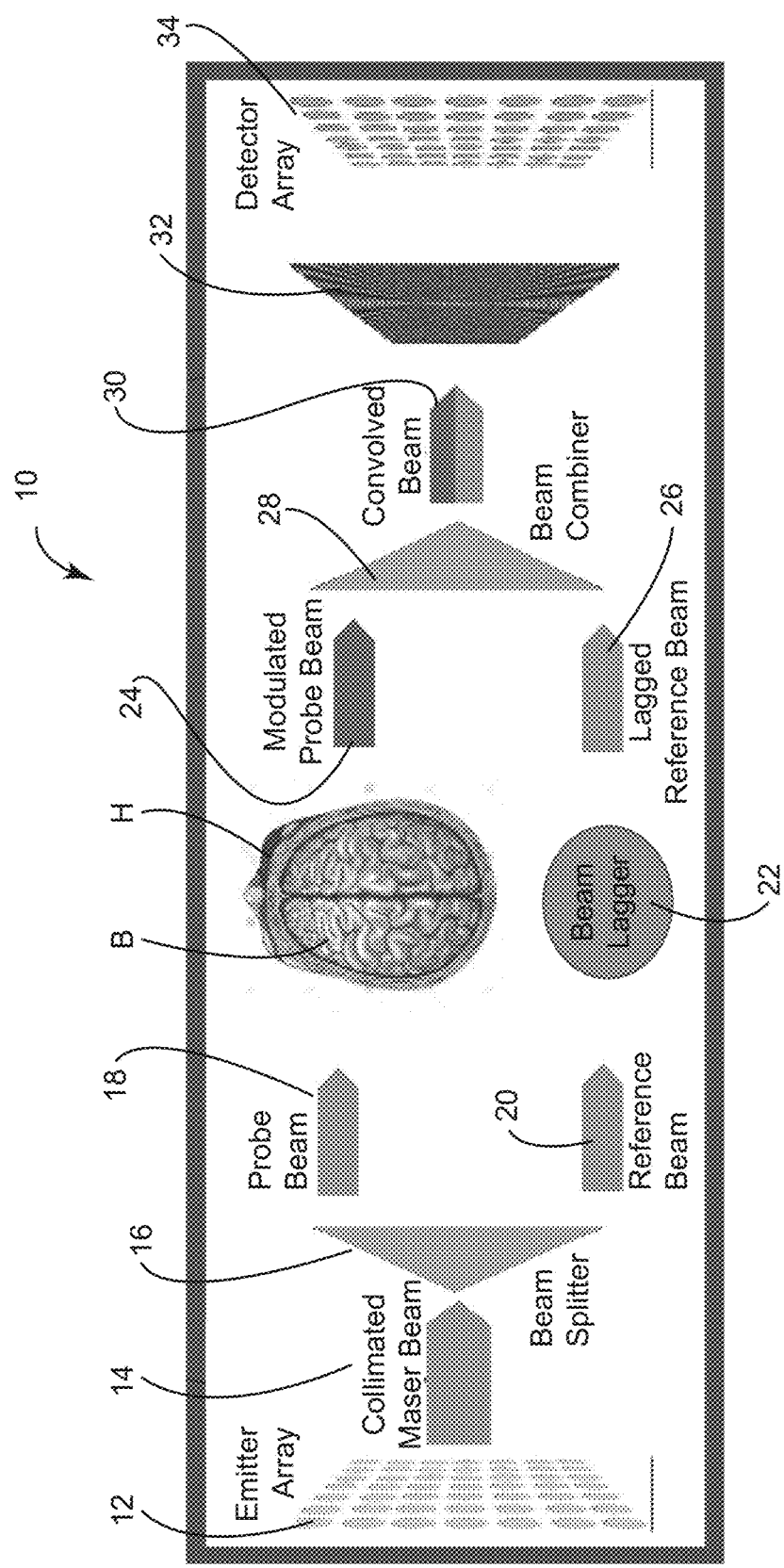
FIG. 7 is a diagram illustrating the components and operation of an exemplary system utilizing MASER interferometry and synthetic aperture techniques to generate an energy activity map of a biological object, in which a phased array detector constructed in accordance with the invention may be used.

A phased array detector 34 constructed in accordance with the invention is configured to detect the intensity across an interference pattern 32 of a convolved MASER beam 30 for the purpose of MASER interferometry, using synthetic aperture techniques to generate a three-dimensional energy activity map of a biological object. FIG. 7 shows the components of an exemplary energy mapping system 10 in which the phased array detector 34 may be used.

Referring to the exemplary embodiment illustrated in FIG. 7, the activity mapping system 10 is a real-time MASER diffraction-limited interferometer. The activity mapping system shown in FIG. 7 includes an emitter array 12 that outputs a collimated MASER beam 14. The emitter array 12 is a phased-array of a plurality of emitters that outputs a mode-locked, coherent MASER beam which is then passed through a collimator (not shown). The characteristics of the MASER beam are desirably tunable. A beam splitter 16 is provided to split the collimated MASER beam into a probe beam 18 and a reference beam 20. The probe beam 18 passes through the biological object which in FIG. 7 is a human head H. The energy activity mapping is intended to be for the brain B within the head H, or for a portion of the brain. The passing of the probe beam 18 through the head H and brain B results in a modulated probe beam 24. Contemporaneously, the reference beam 20 passes through a beam lagger 22 which delays the reference beam 20 the same amount as the probe beam 18 is delayed passing through the head H. This results in a lagged reference beam 26. The modulated probe beam 24 and the lagged reference beam 26 are combined using a beam combiner 28. The combined beams result in a convolved beam 30 which exhibits a time-shifting interference pattern as depicted by reference number 32 in FIG. 7. A phased array of detectors 34 dynamically senses the interference pattern 32 using synthetic aperture interferometry techniques. De-convolution of the interference pattern quantifies changes in phase, modulation, amplitude and lag between the two beams 18 and 20.

The emitter array 12 in the exemplary embodiment is described in the above incorporated, co-pending application Ser. No. 17/148,215 entitled "Thin Film MASER Emitter and Thin Panel Phased Array of Emitters," by James Joseph Cohen and Emad N. Eskandar, filed on even date herewith and incorporated by reference herein. The incorporated co-pending patent application describes a unique combination of thin epitaxial diamond film implanted with nitrogen ions in combination with other component layers to enable the fabrication of a thin panel, phased-array of MASER emitters, which uses Q-switching to form the tunable, mode-locked continuous wave MASER beam.

Briefly, starting at the back of the emitter elements, the layered components are as follows: 1) A thermo-electric Peltier slab is oriented next to an LED layer to control the temperature of the LED layer. 2) A thin high-output Light Emitting Diode (LED) layer provides the photon pump. 3) A first layer of alternating layers of dielectric polymers to reflect the microwaves and provide the sides of the resonator cavity. 4) A layer of CCD (charge Coupled Device) controlled nematic molecules deposited unto the gain medium, which functions as a Q-switch and provides an interface for addressable control of the emission and entrainment of coherent emissions across the array. 5) The gain medium is composed of a thin-film of epitaxial diamond ion-implanted with nitrogen. 6) A second layer of the alternating layers of dielectric polymers to reflect microwaves and provide the other side of the resonator cavity.

The microwave wavelengths are orders of magnitude greater than the dimensions of a single emitter. The alternative approach of housing the entire flat panel array in a physical resonant cavity, would severely limit its practical application, and being a rigid physical structure, would also limit the potential for tunability.

As shown in FIG. 7, the MASER emitter array 12 takes the form of a panel, which is operated to generate MASER emissions that are stable and have long length coherence. The exemplary embodiment of the MASER emitter array in the incorporated application is formed by a multi-element phased array having a plurality of 2-dimensional emitters as a homo-structure, layered into a multi layered 3-dimensional assembly with orthogonal spacing offset by the desired resolution of the interferogram. This assembly is manufactured using an epitaxial technology or similar means to generate an implantable zero dangling-bond gain medium, that can be ion milled and implanted to achieve transitional vacancies at the desired masing frequencies. Further, this stacked emitter forms an addressable synthetic-aperture emitter, transparent to the optical pump except for the quantum lattice transition idealized by the ion implantation admixture.

In a typical MASER or laser, the gain media is contiguous, and all of the active moieties are essentially in one unit (such as a doped crystal), potentially participate in the process of amplification. Coherent emission is achieved by stimulated emission through a population inversion. In essence, the gain media, composed of a great plurality of coupled re-radiative components are stimulated with a pump of energy. Thereafter, a preferred step of energy conversion is selected by stimulating the transition in a uniform manner. This causes a cascade of emission from the gain media in an energy signature and vector consistent with the overall resonation of the gain media. Other radiative transitions are minimized and occupy a fractional component of the energy conversion. The overall effect is that the light emission appears to be radiating from a single radiative element. The photon wavefront is coherent and is synthesized from the overall emission topology.

In the incorporated co-pending application Ser. No. 17/148,215, entitled "Thin Film MASER Emitter and Thin Panel Phased Array of Emitters" by James Joseph Cohen and Emad N. Eskandar, filed on even date herewith and incorporated by reference herein, a different approach is used to generate coherent emissions from the array 12 of discrete emitters in which the Q-switch layer is mated to the active diamond layer, both of which are within the resonant cavity of each emitter. The Q-switch layer is transparent to photons (in the visible range) pumped from the LED layer, but selectively scatters photons in the microwave range of interest. Depending on its state (low Q or high Q), the switching layers selectively interferes with microwave transmission, favoring coherent emission across the entire array, and dispersing the rest. It is this effect by which a quasi 2-dimensional emitter/gain media can produce a diffraction limited beam of consequence.

Provided that the wave propagating emitter is stable and controllable, the Q-switch layer is used to generate a coherent beam through the combined emissions of the individual emitters. Before use, the array 12 of microwave emitters is calibrated. Once the array 12 is powered and stable, the Q-switch layer of each element is individually flipped from low-Q (nonpermissive) to high-Q (permissive) to determine the time needed to reach the masing threshold. This is a stable quantity reflecting particular features of each element. Coherent emissions always start at the lowest point of the waveform. Once the timing is ascertained, the Q-switch layer of each element is programed with a small delay specific to that element. The slowest element has zero delay while faster elements have proportionately longer delay. Subsequently, coherent emission is initiated by first turning all the switches to low-Q (nonpermissive). At the desired time, the individual emitters are flipped to high-Q (no disruption) with the programmed delays so that the faster elements begin emission at the same time as the slowest element. In this fashion, coherent emission from all the arrays starts at the same time. Since MASER emission always starts at the lowest point of the waveform, they are in-phase and the resultant beam, or wave-front, is coherent.

Prior to splitting the MASER beam, the beam is introduced into a collimator, such as a gaussian telescope composed of geometric optics. This telescope is fabricated to ensure that the overall divergence and coherence of the collimated MASER beam 14 is adequate to transverse the free space between the emitter array 12 and the phased array detector 34 without decohering.

The system 10 in FIG. 7 includes a geometric optic 16 (i.e. beam splitter 16 in FIG. 7) that serves to split the collimated MASER beam 14 into two coherent, mode-locked beams. These beams 18, 20 are identified as the probe beam 18 and the reference beam 20. Being derived from a singular beam split into two components, these beams 18, 20 would normally remain singularly coherent over a free space distance corresponding the theoretical coherence length. Splitting the collimated MASER beam 14 into two beams 18, 20 having the same wavelength and phase/polarization coherence requires a grating 16 or geometric optic 16 made out of an optical grade polymer. The beam splitter 16 can be fabricated from dielectric materials and organized into geometries suitable for scraping. Poly-tetrafluoroethylene bulk material should be suitable. Successful beam splitting can be determined by analyzing the frequency, intensity, and coherence length of the probe beam 18 and the reference beam 20 and ensuring that its characteristics are adequate. Prior to splitting the MASER beam, the beam is introduced into a gaussian telescope composed of geometric optics, which serves as a collimator. This telescope is fabricated to ensure that the overall divergence and coherence of the MASER is adequate to transverse the free space between the emitter and the phased array detector 34 without decohering. The system 10 also incorporates the mentioned geometric optic 16 that serves to split the MASER beam into the two coherent and phase locked beams, namely the probe and reference in FIG. 7. Being derived from a singular beam split into two components, these beams would remain singularly coherent over a free space distance corresponding the theoretical coherence length. Splitting the MASER beam into two beams having the same wavelength and phase/polarization coherence requires a grating or geometric optic made out of an optical grade polymer. The beam splitter 16 can be fabricated from dielectric materials and organized into geometries suitable for scraping. Poly-tetrafluoroethylene bulk material should be adequate. Successful beam splitting can be determined by analyzing the frequency, intensity, and coherence length of the probe and reference beam and ensuring that its characteristics are adequate.

Still referring to FIG. 7, the reference beam 22 must be delayed in order to remain in phase with the modulated probe beam 24. A suitable beam lagger 22 is a pane of uniform material resulting in a delay similar to the delay caused by the head H and brain B. The performance envelope of the emitter array 12 and the detector array 34 requires a fully analog means to combine the modulated probe beam 24 and lagged reference beam 26. The beam combiner 28 should be engineered to preserve the coherence of the beams 24, 26 and not introduce aberrations that would interfere with data deconvolution.

Still referring to FIG. 7, generation of the convolved beam is accomplished with the beam combiner 30. The performance envelope of the emitters and detectors adequate to the chosen specification requires fully analog means to combine the modulated probe 24 and lagged reference beam 26. This beam combiner 30 is engineered to preserve the coherence of the beams and not introduce aberrations that would interfere with data deconvolution. The beam combiner 30 is identical to the beam splitter 16 (e.g. a geometric optic) and interposed into the beam paths in the opposite manner of the beam splitter.

The detector array 34 is specifically designed for the detection of MASER intensity in a dynamic manner and sufficiently fast and sensitive to resolve interference patterns 32 in the convolved beam 30. Passage through various substances can result, e.g., in phase distortion of the probe beam 18 relative to the reference beam 20. Combination of the modulated probe beam 24 and the lagged reference beam 26 results in an alteration of the interference pattern 32 in the convolved beam 30. The elements of the detector array 34 are arranged in two layers offset by an orthogonal offset as described in more detail below. The orthogonal offset provides a spatially disparate sensing discriminator. The offset detector elements are otherwise identical, such that spatially offset detector elements permit correspondence to a time difference measured in decades of picoseconds. This architecture permits real time sensing of intensity data otherwise indistinguishable from the noise background.

Figure 8:
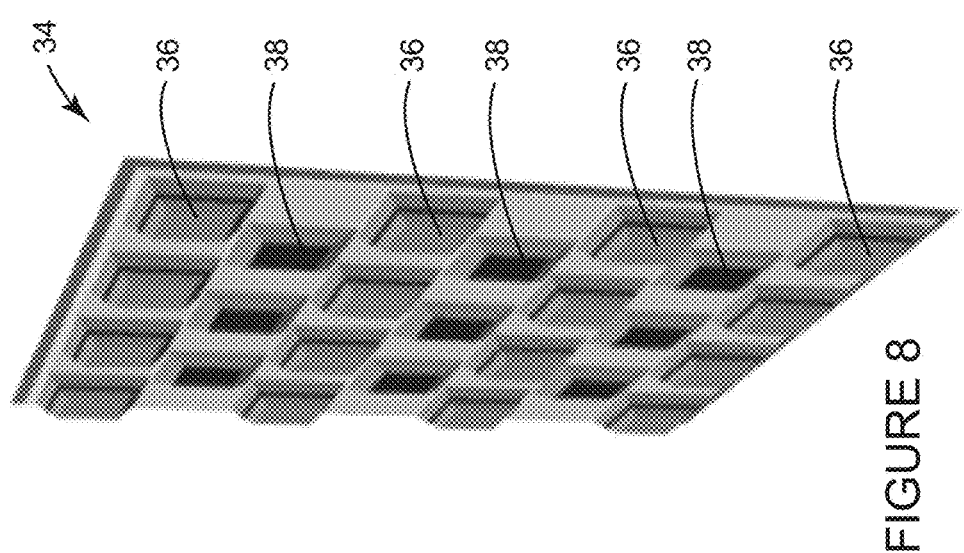
FIG. 8 is schematic drawing showing a portion an exemplary phased array detector constructed in accordance with the invention.

FIG. 8 illustrates a portion of an exemplary phased-array detector 34 constructed in accordance with the invention. The array 34 of detector elements are arranged in a first planar layer 36 and in a second planar layer 38. The second planar layer 38 that is parallel to the first planar layer 26. The detector elements 38 in the second planar layer 38 are offset in three dimensions from the detector elements 36 in the first planar layer 36. Each of the detector elements in the array 34 is exposed to the forward perpendicular direction and is able to detect the intensity of the convolved beam 30 directly. It is expected that the array 34 will contain $10^2$ to $10^6$ detector elements, such that would be appropriate to refer to the detector elements as pixels.

Figure 9:
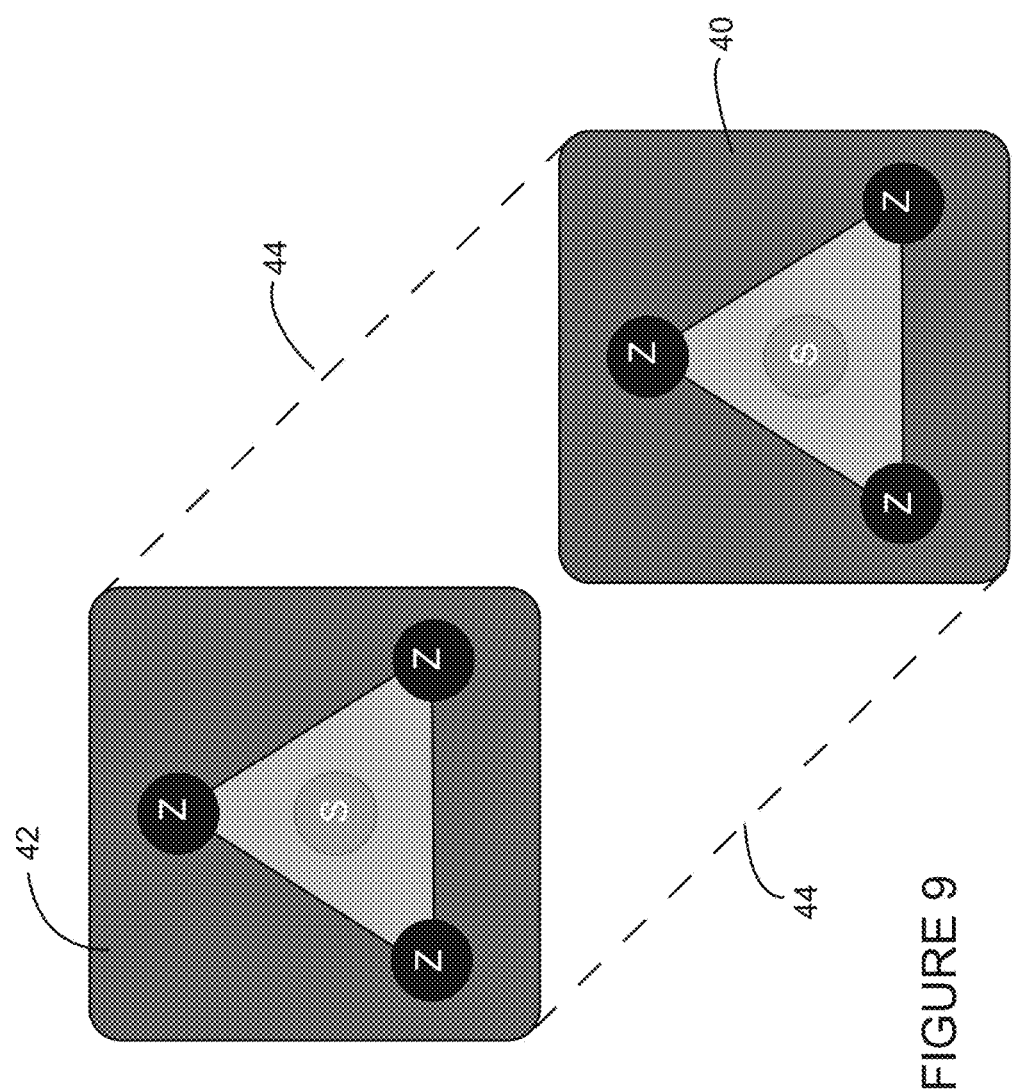
FIG. 9 is a view schematically illustrating offset, zero biased Schottky detector elements for use in connection with the exemplary embodiment of the invention.

FIG. 9 schematically illustrates a detector element 40 is the first planar layer 36 and a detector element 42 in the second planar layer 38. The dashed lines 44 represent the three-dimensional offset. The offset allows for developing a spatially disparate sensing discriminator. The offset detector elements 40,42 are physically identical, with the spatial offset selected to permit correspondence to a time difference measured in decades of picoseconds. As mentioned, this architecture permits permit real time sensing of data otherwise indistinguishable from the noise background.

The detector elements 40, 42 consist of zero-bias Schottky detector diodes. The diodes should be selected to sufficient sensitivity to reliably detect the MASER radiation of interest. The Schottky detector diodes can be biased with Zener diodes to provide the necessary stability for precise edge-detection. The repeatability and stability of the jitter permits real time data acquisition in the frequency of interest.

Figure 10:
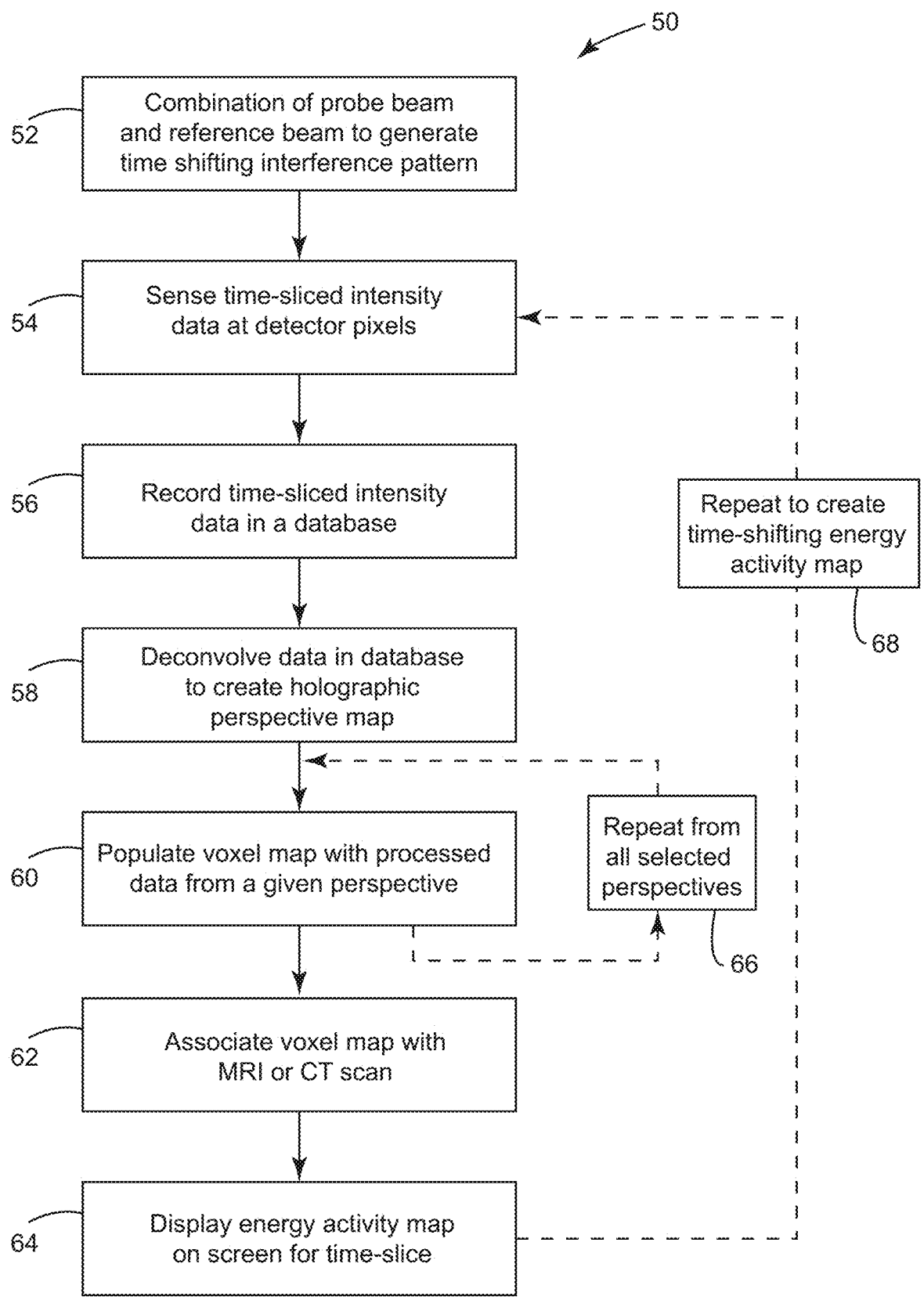
FIG. 10 is flow chart illustrating the steps involved in using a phased detector array to generate time-shifty energy activity maps of a biological object from the detection of a time shifting interference pattern using synthetic aperture techniques.

The detector array 34, as mentioned, is specifically designed for the detection of MASER energy intensity with sufficient speed and sensitivity to resolve interference patterns. Referring to FIG. 10, exemplary steps of involved with the process of generating an energy activity map of a biological object or portion of the biological object are illustrated. As discussed above, the overall method begins by emitting a beam of coherent MASER radiation and passing the emitted beam through a collimator. The collimated beam of coherent MASER radiation is then split into a probe beam and a reference beam. The probe beam is passed through a biological object to create a modulated probe beam and the reference beam is simultaneously passed through a uniform substance resulting in a delay of the reference beam similar to that of the probe beam caused by the biological object in order to generate a lagged reference beam. The lagged reference beam and the modulated probe beam are combined to create a convolved beam characterized by a time-shifting interference pattern. Block 52 in FIG. 10 illustrates the step of combining the modulated probe beam and the lagged reference beam to generate a time-shifting interference pattern. As mentioned above the combination or convolution of the beams is accomplished via an analog beam combiner. Block 54 in FIG. 10 illustrates that time-sliced intensity data of the interference pattern in the convolved beam is detected by the plurality of detector elements in the phased array detector. The plurality of detector elements in the phased array detector are arranged in a first planar layer and in a second planar layer that is parallel to the first planar layer and offset in three dimensions from the detectors elements in the first planar layer, as described above. Then, see block 56, time-sliced intensity data of the interference pattern detected by the plurality of detector elements is recorded in a database. A computer is programmed to de-convolve the time-sliced intensity data of the interference pattern, see block 58. It will often be desirable, as the first step of deconvolution, to apply a Fast Fourier Transform in order to isolate one or more wavefront frequencies for processing. Pseudo real-time deconvolution may require running parallel Fast Fourier Transforms (FFTs), maximally optimized for rapid execution. These are ASIC (application specific Integrated Circuit) components providing digital output. The number of discrete devices and channels coordinates to the jitter maximum of both the emitters and the detectors. Parallel CPUs and data storage subsystems are provided to ensure that time-sliced deconvolution is not recursive nor gapped thereby preventing decoding artifacts from being introduced.

The result of the deconvolution results in processed data that quantifies changes in one or more of phase, modulation, amplitude, and lag between the modulated probe beam and the lagged reference beam and the creation of a holographic perspective map, see block 58. This projection is holographic in nature as it is a projected volume illumination from a distilled interferogram.

A voxel map is populated with the processed data for the slice of time from the given holographic perspective (block 60), and this is repeated from multiple holographic perspectives in accordance with a synthetic aperture algorithm to improve the resolution, (block 66).

The populated voxel map is then associated with or overlayed on an image generated by an MRI or CT scan to create a three-dimensional energy activity map for the given time slice of the biological object or a portion of the biological object (block 64). The three-dimensional energy activity map for the given time slice is then displayed (block 64) for immediate review or stored for later analysis. The method can be repeated for subsequent time slices to generate time-shifting, three-dimensional energy activity maps (block 68).

The method 50 in FIG. 10 can be used to acquires data in a variety of biomedical applications, including for example data pertaining to the function and performance of in-vivo mapping of brain activity as potentiated at the axonal interfaces. The method is capable of generating data rich three-dimensional energy activity maps of the brain B. In some embodiments of the system disclosed in incorporated co-pending application Ser. No. 17/148,120, entitled "Acquisition of Interferometric Recordings of Brain and Neuron Activity by Coherent Microwave Probe with Therapeutic Activation, Inactivation, or Ablation of Molecular, Neuronal or Brain Targets." by Emad N. Eskandar and James Joseph Cohen, filed on even date herewith and incorporated by reference herein, the energy activity maps are used to provide feedback as to the effectiveness of neuromodulation (e.g. enervation or energization via Rabi coupling) of molecules within specific voxels.

There are many contemplated uses of the phased array detector and the method of energy activity mapping of a biological object using MASER interferometry described herein.

For example, the detector and the method can be used to implement MASER interferometry to study and characterize patterns of molecular activation in healthy subjects and in those suffering from brain disorders; to study and characterize activation of specific patterns of molecular activation in voltage-gated ion channels, ligand gated ion channels, and G receptor coupled channels; to study patterns of neural activity associated with normal brain function in sensory, cognitive and emotional tasks; to study characterize, and diagnose patterns of neural activity associated with neurodegenerative disorders and protein accumulation including Parkinson Disease (synuclein) and Alzheimer Disease; to study, characterize, and diagnose patterns of neural activity movement disorders such as tremor, dystonia, and tics; to study, characterize, and diagnose disordered brain activity in epilepsy, migraine headaches, tinnitus and chronic pain; to study, characterize, and diagnose patterns of neural activity in Psychiatric disorders including obsessive-compulsive disorder (OCD) major depression, bipolar depression, schizophrenia, generalized anxiety, post-traumatic stress disorder (PTSD), phobias, and panic attacks; and to study, characterize, and diagnose patterns of neural activity in behavioral disorders including substance addiction, pathological gambling, obesity, attention deficit hyperactivity disorder (ADHD), internet gaming disorder and autism.

In addition, it is contemplated that the phased array detector and the method of energy activity mapping of a biological object using MASER interferometry described herein can be used to provide real-time or near real-time feedback when MASER radiation is used for neuromodulation to treat movement disorders including tremor, dystonia, and tics (Tourette's); to treat disorders of brain activity including epilepsy, migraine headache, tinnitus and chronic pain; to treat psychiatric disorders including obsessive-compulsive disorder (OCD) major depression, bipolar depression, schizophrenia, generalized anxiety, post-traumatic stress disorder (PTSD), phobias, and panic attacks; to enhance recovery of movement, speech, short-term memory, long-term memory and cognition following brain injury or stroke; to enhance memory in Alzheimer disease; and to promote disruption and absorption of protein aggregates including synuclein in Parkinson disease and beta amyloid in Alzheimer disease.

It is further contemplated that the phased array detector and the method of energy activity mapping of a biological object using MASER interferometry described herein can be used to provide real-time or near real-time feedback when MASER radiation is used to ablate discrete brain targets for the treatment of intrinsic or metastatic brain neoplasms, epilepsy, arteriovenous malformations, and essential tremor.

What is claimed is:

1. A phased-array MASER (Microwave Amplification by Stimulated Emission of Radiation) detector for synthetic aperture interferometric three-dimensional imaging comprising:
    an array of detector elements arranged in a first planar layer and in a second planar layer that is parallel to the first planar layer and in which the detector elements are offset in three dimensions from the detector elements in the first planar layer, wherein each detector element is Schottky detector diode that detects an intensity of MASER radiation.

2. The phased-array MASER detector for the synthetic aperture interferometric three-dimensional imaging recited in claim 1 wherein each said Schottky detector diode is zero biased.

3. The phased-array MASER detector for the synthetic aperture interferometric three-dimensional imaging recited in claim 2 wherein each Zener diode of Zener diodes are used to zero bias each said Schottky detector diode.

4. The phased-array MASER detector for the synthetic aperture interferometric three-dimensional imaging recited in claim 1 wherein an offset orthogonal to the first planar layer of detectors and the second planar layer of detectors is such that spatially offset detect elements permit correspondence to a time difference measured in decades of picoseconds.

5. The phased-array MASER detector for the synthetic aperture interferometric three-dimensional imaging recited in claim 1 wherein the array of detector elements in the phased-array MASER detector sense time-sliced intensity of an interferometric pattern formed by a convolution of a probe MASER beam that passes through an object being analyzed and a reference MASER beam.

6. The phased-array MASER detector for the synthetic aperture interferometric three-dimensional imaging recited in claim 1 further comprising:
    a database that stores time-sliced intensity data detected by the detector elements; and
    a computer configured to deconvolve the time-sliced intensity data in the database at least in part by implementing a synthetic aperture imaging algorithm to create a holographic perspective map, to populate a voxel map with deconvolved data from multiple perspectives in the holographic perspective map, and to associate the voxel map with a magnetic resonance imaging (MRI) or computerized tomography (CT) scan to generate an energy activity map for the time-sliced intensity data.

7. A method of energy activity mapping of a biological object using real-time MASER (Microwave Amplification by Stimulated Emission of Radiation) interferometry, the method comprising the steps of:
    emitting a beam of coherent MASER radiation and passing the emitted beam through a collimator;
    splitting of the collimated beam of coherent MASER radiation into a probe beam and a reference beam;
    passing the probe beam through the biological object to create a modulated probe beam and simultaneously passing the reference beam through a uniform substance resulting in a delay of the reference beam similar to that of the probe beam caused by the biological object in order to generate a lagged reference beam;
    combining the lagged reference beam and the modulated probe beam to create a convolved beam characterized by a time-shifting interference pattern;
    detecting time-sliced intensity data of interference pattern in the convolved beam with a plurality of detector elements of a phased array detector, wherein the plurality of the detector elements in the phased array detector are arranged in a first planar layer and in a second planar layer that is parallel to the first planar layer and in which the detector elements are offset in three dimensions from the detector elements in the first planar layer;
    recording the time-sliced intensity data of the interference pattern detected by the plurality of detector elements in a database;
    de-convolving the time-sliced intensity data of the interference pattern to generate processed data that quantify changes in one or more of phase, modulation, amplitude, and lag between the modulated probe beam and the lagged reference beam and to create a holographic perspective map;
    populating a voxel map with the processed data for the slice of time from the given holographic perspective and repeating this step from multiple holographic perspectives in accordance with a synthetic aperture algorithm;
    associating the voxel map with an image generated by a magnetic resonance imaging (MRI) or computerized tomography (CT) scan to create a three-dimensional energy activity map for the given time slice; and
    displaying the three-dimensional energy activity map for the given time slice of the biological object or a portion of the biological object.

8. The method in claim 7 wherein the beam of coherent MASER radiation is generated by a phased emitter array using synthetic aperture techniques.

9. The method in claim 7 wherein the biological object is a brain.

10. The method of claim 7 wherein the de-convolution step involves use of a Fast Fourier Transform and isolating of one or more wavefront frequencies such that the processed data contains data pertaining to the one or more isolated wavefront frequencies.

11. The method of claim 7 wherein the method is repeated for subsequent time slices.

12. The method of claim 7 wherein the method is repeated for subsequent time slices in order to generate and display a time-shifting, three-dimensional energy activity map of the biological object or a portion of the biological object.

* * * * *